(12) United States Patent
Roel Cardama

(10) Patent No.: US 11,944,888 B2
(45) Date of Patent: Apr. 2, 2024

(54) SYSTEM AND METHOD FOR LAUNCHING A BALL ONTO THE GROUND OF A PLAYING FIELD

(71) Applicant: Diego Roel Cardama, Salcedo (ES)

(72) Inventor: Diego Roel Cardama, Salcedo (ES)

( * ) Notice: Subject to any disclaimer, the term of this patent is extended or adjusted under 35 U.S.C. 154(b) by 14 days.

(21) Appl. No.: 17/784,291

(22) PCT Filed: Dec. 10, 2020

(86) PCT No.: PCT/ES2020/070777
§ 371 (c)(1),
(2) Date: Jun. 10, 2022

(87) PCT Pub. No.: WO2021/116521
PCT Pub. Date: Jun. 17, 2021

(65) Prior Publication Data
US 2022/0347545 A1     Nov. 3, 2022

(30) Foreign Application Priority Data

Dec. 10, 2019  (ES) .................................. P201931093

(51) Int. Cl.
*A63B 47/00*     (2006.01)
*A61L 2/10*      (2006.01)
(Continued)

(52) U.S. Cl.
CPC .............. *A63B 69/409* (2013.01); *A61L 2/10* (2013.01); *A61L 2/202* (2013.01); *A63B 47/002* (2013.01);
(Continued)

(58) Field of Classification Search
CPC ..... A63B 69/002; A63B 69/409; A63B 69/38; A63B 69/40; A63B 69/406; A63B 47/002; A63B 47/008
(Continued)

(56) References Cited

U.S. PATENT DOCUMENTS

| 4,699,386 A | 10/1987 | Carzino |
| 11,077,352 B1 * | 8/2021 | Greene, Jr. .......... A63B 69/406 |

(Continued)

FOREIGN PATENT DOCUMENTS

| CN | 109350943 A | | 2/2019 |
| DE | WO2005023380 | * | 3/2005 ........... A63B 69/002 |

(Continued)

OTHER PUBLICATIONS

International Search Report (with English Translation) and Written Opinion dated Apr. 23, 2021, in connection with corresponding International Patent Application No. PCT/ES2020/070777; 11 pages.

*Primary Examiner* — John E Simms, Jr.
(74) *Attorney, Agent, or Firm* — Maier & Maier, PLLC

(57) ABSTRACT

System and method for launching a ball onto the ground of a playing field. The system includes an outlet chamber configured to receive the ball therein; an outlet conduit or frame configured to contain the outlet chamber and allow the same to move through the outlet conduit towards a second position on the ground; movement capability of the outlet chamber, connected to and configured to move the outlet chamber between at least the first position and the second position, where the outlet chamber includes an outlet mouth and launching means for launching the ball arranged in the outlet chamber. A field including the system is also described.

16 Claims, 6 Drawing Sheets

(51) Int. Cl.

| | |
|---|---|
| *A61L 2/20* | (2006.01) |
| *A63B 47/02* | (2006.01) |
| *A63B 69/00* | (2006.01) |
| *A63B 69/40* | (2006.01) |
| *A63B 71/00* | (2006.01) |
| *A63B 71/02* | (2006.01) |

(52) U.S. Cl.
CPC ............ *A63B 47/02* (2013.01); *A63B 69/002* (2013.01); *A63B 69/406* (2013.01); *A63B 71/0054* (2013.01); *A63B 71/02* (2013.01); *A63B 2071/009* (2013.01)

(58) Field of Classification Search
USPC .......................................................... 473/438
See application file for complete search history.

(56) References Cited

U.S. PATENT DOCUMENTS

| | | | |
|---|---|---|---|
| 2005/0233818 A1* | 10/2005 | Chen | A63B 47/002 473/135 |
| 2006/0121996 A1* | 6/2006 | Clifford | A63B 63/00 472/92 |
| 2016/0262351 A1* | 9/2016 | Hamill | A01K 15/027 |
| 2016/0310817 A1* | 10/2016 | Yeager | A63B 69/406 |
| 2017/0136337 A1* | 5/2017 | Lee | A63B 69/40 |
| 2017/0348582 A1* | 12/2017 | Cho | A63B 69/40 |
| 2020/0398139 A1* | 12/2020 | Harley | A63B 69/406 |

FOREIGN PATENT DOCUMENTS

| | | | | |
|---|---|---|---|---|
| JP | 2018122063 A | | 8/2018 | |
| KR | 20120080738 | * | 7/2012 | ........... A63B 47/002 |

* cited by examiner

SYSTEM AND METHOD FOR LAUNCHING A BALL ONTO THE GROUND OF A PLAYING FIELD

TECHNICAL FIELD

The present invention relates to a system and a method for launching a ball onto the ground of a playing field. Likewise, the present invention relates to a playing field comprising a system for launching balls onto the ground of the playing field. In one of the more preferred embodiments thereof, the present invention relates to methods and devices for throwing balls onto a football field, for example, to reintroduce a football onto the field, launching the ball close to the post and preferably in a direction and/or towards a desired position and preferably with a trajectory that are desired when required in order to allow players to play with the ball on the field.

BACKGROUND

There is a great plurality of sports, i.e., matches, which are played on corresponding types of fields using one or more corresponding balls. Typically, in these types of sports when a ball leaves the playing field, or when the ball enters one or more specific areas, the ball usually must be reintroduced onto the field so that the player or players of the sport can continue to play with the ball. For example, during a football match there often exists the need to launch a ball in the small area or towards the corner area each time a ball must be (re)introduced onto the grass so that the players can continue with the match.

In sports such as football, (re)introducing balls onto the grass during the match is done by ball boys who tend to adjust the speed of their own actions according to their thoughts on the positive impact that this speed may have on the result needed by the team that the ball boys support. For this reason, a system is needed that standardises the speed of (re)introducing the balls onto the field, or at least offers control of said speed to the match referees, to ensure that the overall procedure is fairer for both teams and to ensure that unnecessary lost time is avoided during the match. Likewise, this system must have another very important property: that it is safe for the players and/or the referees and/or any other person who may be running, jumping, etc. on the playing field.

In the prior art, there are two categories of systems for introducing balls onto a playing field, and these two categories exhibit some very important differences between them that are related to the position and structure of the system, or at least to the position and structure of the final portion of the system which introduces the ball onto the field, with respect to the level of the field surface. The first category includes surface systems, in other words, systems wherein said final portion of the system that introduces the ball onto the playing field is constantly on the surface, i.e., it is above the level of the upper surface of the ground of the playing field. An example of these first category systems is described in the US patent application with publication number US2017/0348582A1. This system, like the other first category systems, has means for launching a ball and said means are constantly above the ground of the field. For this reason, these means, which are situated in a head that forms the final end of the system through which the ball exits and is launched and introduced onto the field, are usually supported by a fixed and constantly superficial structure which can comprise, for example, one or more stakes that constantly protrude from the ground. It is obvious that a structure of this type could constantly prevent spectators from observing the match, and it could be dangerous for players who might mistakenly or accidentally touch and damage it, especially when said structure is substantially close to or within the area where the players play. Consequently, the vast majority of first category systems, although they may be considered suitable for launching a ball, can also be considered dangerous for players and problematic for any person or party who is interested in having a playing field with as few fixed surface structures as possible.

Moreover, there is the second category of systems for introducing balls onto the field, this category being characterised in that the systems thereof, or at least the final portions of the systems through which the balls exit onto the field, are not constantly above the ground but below it. However, these second category systems are characterised by an additional fact: they do not have means for launching the ball and for controlling and dictating the trajectory of the ball when it is launched. In other words, these second category systems can be substantially underground, and for this reason they pose less risk of players accidentally touching the systems. Nevertheless, the main functionality of second category systems is to introduce the ball onto the field without launching it since these systems do not have the necessary means for launching the ball and controlling the trajectory thereof. Two examples of underground systems that are configured to introduce a ball onto the field without launching it and without controlling the trajectory thereof onto the field are described in Chinese patent with publication number CN106512361B and in Chinese utility model with publication number CN206563467U. The figures in these two Chinese documents show systems that have an underground conduit through which balls pass, and this conduit ends in a flat platform that is not covered by other elements and is configured to receive on the surface thereof a ball at a low point in the ground and vertically lift the ball to the surface of the playing field by introducing the ball at a second point that is vertically above the first point and at the level of the ground surface. A player can go to this second point to collect the ball from there. Then, by means of the platform of the system, the ball is introduced on the ground, but it is not launched onto this ground, and the trajectory of the ball cannot be controlled and, as a result, the ball cannot be launched in a required direction, e.g., towards the goalkeeper or another player in a football match. Likewise, it should be noted that in second category systems the platform moves vertically by means of a lifting tube that is vertical, i.e., it is perpendicular to the surface of the field, and when the platform is inside the ground, e.g., when the platform is at the first point for collecting the ball, the upper mouth of the lifting tube remains open forming a hole and this implies that there is a danger that a player will fall into said hole. As such, second category systems generally lack the functionality of being able to launch the ball in a controlled way, and they are not safe for the players.

As mentioned, the prior art does not describe systems, and corresponding methods and playing fields, that offer a solution to the problem of how to obtain a system that is safe and at the same time can introduce the ball by launching it and offering the functionality of controlling the trajectory of the ball. The present invention solves this problem.

SUMMARY

To solve the problem posed, the present invention presents a system, a method and a playing field that are suitable for introducing the ball by launching in a controlled manner and with a controllable trajectory onto the surface of the field, and at the same time keeping the players safe, without having, producing or requiring the existence of holes in the field, which are constantly left open, for fixed structures that constantly protrude from the ground or pose other serious dangers.

The present invention in a first aspect is a system for launching a ball onto the ground of a playing field, wherein the system comprises:

An outlet chamber that is configured to receive a ball therein when the outlet chamber is in a first position that is under the ground;

An outlet conduit that is configured to contain the outlet chamber and allow the latter to move through the outlet conduit towards a second position that is on the ground and in which the ball can exit from the outlet chamber to the ground;

Movement means of the outlet chamber, connected to and configured to move said outlet chamber between at least the first position and the second position, wherein the outlet chamber comprises an outlet mouth and launching means for launching the ball arranged in said outlet chamber and configured to apply pressure on the ball forcing it to exit the outlet chamber and enter onto the ground by means of the outlet mouth.

Optionally, the outlet conduit is or comprises a structure (frame). Said structure can be an outlet structure (frame). Preferably, the first position is under the ground. This can be when for example the system is installed on a playing field. Preferably, the second position is on the ground. This can be when for example the system is installed on a playing field.

All the elements of the system according to the first aspect of the invention are essential elements that work together to ensure that the system is safe for the players of the match and ensure that the system can launch a ball efficiently, reliably and in a well-controlled manner A first feature of the system is that it comprises an outlet chamber that is configured to receive the ball therein when the outlet chamber is in a first position that is under the ground, i.e., below the level of the ground surface on which the players play. This first feature substantially differentiates the present invention from both categories of the systems of the state of the art that are described above in this specification. In the present invention, the system, given that it comprises a chamber that can receive the ball therein and lift it to ground level, differs from the first category systems of the state of the art, which have an outlet chamber which is fixed and/or is constantly on the ground. Likewise, the system of the present invention, given that it comprises said outlet chamber, differs from the second category systems of the state of the art, which comprise simple platforms that receive and lift the ball and do not comprise complete chambers which receive the ball therein and are fully lifted, thus lifting the ball and protecting the latter against adverse factors, e.g., weather conditions such as strong winds.

As mentioned above, the outlet chamber comprises an outlet mouth and launching means for launching the ball, and these elements share some very important synergistic effects. The launching means, given that they are comprised in the outlet chamber, can be lifted and lowered by lifting and lowering the outlet chamber, and thus can be introduced onto the field only when the ball is to be introduced and launched onto the field. Likewise, the launching means are substantially protected by the rest of the chamber which can protect said launching means against various adverse factors such as meteorological conditions, e.g., rain and strong winds, and voluntary or unintentional impacts by objects such as pieces of grass, particles of dirt, or other objects such as debris left by people or moved through the air. For all these reasons, optionally and preferably, the launching means are situated at least partially inside the chamber, and more preferably completely inside the chamber, in which case no portions of said means protrude from the chamber. In these cases, the launching means are protected by the chamber in a way similar to the way in which the ball is protected by the chamber when it is inside the same. Likewise, it should be noted that the outlet mouth is used so that the ball can exit the chamber when it is launched by the launching means, when the chamber is in said second position. It is clearly understood from the foregoing that when the outlet chamber is in said second position, the outlet mouth, or at least the portion of said mouth through which the ball exits, is on the ground, i.e., it is above the level of the upper surface of the ground of the playing field where the match takes place. Likewise, it is important to mention that the outlet mouth and the launching means share important synergistic effects, which are as follows.

A first effect is that the trajectory of the ball that is launched, due to the pressure it receives from the launching means, can be affected by the outlet mouth, especially when said launching means accidentally arrange the ball towards the edges of said outlet mouth. This can happen for example when there is an error or malfunction in the launching means or when these means are not used or are not configured correctly by the user of the system. In these hypothetical cases, the outlet mouth would affect, at least partially, the final trajectory of the ball and prevent the ball from being launched in a completely undesired direction, e.g., towards a player who would not anticipate the ball being launched towards them due to a malfunction or error in the launching means. Another possible synergistic effect is related to the fact that the outlet mouth can generally function as an air duct, and for this reason the air pressure in the chamber can increase when the launching means are activated, pushing the ball which can be released towards said outlet mouth, and in this case, the force under which the ball is launched onto the field is affected by the pressure applied by the launching means, and it can also be affected and/or increased due to the possible shape and/or exact position of the outlet mouth. Considering the above, there is an understanding that it is important that the presence of the launching means in the system be accompanied by the presence of the outlet mouth and that both are comprised in the outlet chamber.

As mentioned above, the system of the first aspect of the invention comprises the outlet conduit and the movement means of the outlet chamber. In the present invention, the outlet conduit obviously has dimensions and a shape that allow the displacement of the outlet chamber between at least the first position and the second position. Likewise, optionally and preferably, the outlet conduit is vertical, i.e., perpendicular to the surface of the ground where the match takes place and on which the second position is located. This optional configuration makes it easy to install the system. In non-limiting examples, the outlet conduit is a conduit that comprises, or is made of, a plastic material, such as PVC (polyvinyl chloride), or a metal such as stainless steel or aluminium.

It is obvious from the foregoing that the outlet conduit has a shape and dimensions that are suitable for the chamber to be able to move between the first position and the second position. Optionally and preferably, when the outlet chamber is in the first position, the entire outlet chamber is substantially under the ground, i.e., under the upper surface of the ground surrounding it and optionally next to the outlet conduit. This makes it so that the outlet chamber, when it is in the first position and not launching the ball, is not an obstacle in the field. For the same reason, optionally and preferably, the outlet conduit is completely below the surface of the field, i.e., the upper end of the outlet conduit does not protrude from the surface of the playing field. Likewise, optionally and preferably, the outlet chamber in the system comprises a finishing part that forms the upper stop of the outlet chamber and has an upper surface which is configured to have a similar texture and be level with the ground surrounding it and it limits said upper surface when the rest of the outlet chamber is under the ground. Thus, on the one hand, it provides the advantage that the system is hidden and safe without impeding the match when the ball is not introduced, and on the other hand, it provides the advantage that the upper stop prevents a hole from forming in the field which could be dangerous for the players. In the optional case that the ground, i.e., the upper surface of the ground of the playing field, comprises grass or is finished with grass, the finishing part optionally comprises or is also a piece of grass, preferably of the same type as the grass of the ground, so that the texture of the finishing part is similar to the texture of the field. This improves the safety and quality of the system and makes it so that the system does not impede the match.

The movement means of the outlet chamber are suitable, i.e., configured, to be able to move the outlet chamber between the first position and the second position, thus implying that the movement means must have sufficient power to move, i.e., lift and lower, the outlet chamber, even when the latter comprises the ball and the launching means. Optionally and preferably, the movement means comprise an electric motor, and a movement transmission system connected to said electric motor and to the outlet chamber, and configured to transform the rotary movement of the motor into a linear displacement movement of the outlet chamber which moves through the inside of the outlet conduit. The movement transmission system for example can comprise one or more gears, e.g., one or more pinions, connected to a bar which can be connected to the motor in such a way that the motor causes the bar to rotate, and the movement transmission system can also comprise a chain connected to said gear(s) and to the outlet chamber. Preferably and optionally, the movement means comprise an electromechanical system that controls the movement and exact position of the outlet chamber according to instructions from the user of the system, and this electromechanical system can comprise a central processing unit (CPU) which controls said electric motor. To make the system more compact and long-lasting, the movement means are optionally situated inside the outlet conduit.

Optionally, the launching means comprise a pneumatic system that is configured to provide pressurised air or gas in the outlet chamber to launch the ball. This optional feature has the first advantage of being robust or requiring little maintenance, since pneumatic systems generally do not contain as many moving elements as other types of systems, e.g., mechanical systems. In a non-limiting example, i.e., in an optional variation, the pneumatic system comprises at least one nozzle that is arranged in a position inside the chamber, and said position is substantially behind the outlet mouth and the ball which is situated between the outlet mouth and the nozzle when the ball is in the outlet chamber and properly positioned to be launched by the system. Said optional nozzle is fed with pressurised air through a pneumatic conduit which is connected to the same and comprised in the pneumatic system in the same optional variation of the system. Optionally, the pneumatic conduit can be fed through bottles containing pressurised air or gas, or through a pressurised air or gas generation unit, wherein said bottles or pressurised air or gas generation unit can be comprised in the outlet chamber or connected to the same, i.e., connected to the pneumatic system that is comprised in the outlet chamber.

Alternatively, in another optional variation of the system, which is even more preferable, the launching means comprise at least two wheels that can rotate and each one comprises an edge, wherein said wheels are configured so that the ball is inserted therebetween and contacted by said edges, i.e., the ball is in contact with said edges, and they are configured to launch the ball when they rotate, propelling the ball by rotating said edges. Optionally, any of said wheels can be rotated by a corresponding electric launching motor connected to the wheel. The motor is optionally activated and controlled by a motor rotation control system, said control system controlling the rotation of the corresponding wheel which in turn controls, at least partially, the force applied on the ball and the trajectory of the same when the launching means are activated. In the case where there is more than one electric launching motor, each one being connected to the corresponding wheel, the activation and rotation of each motor is optionally controlled independently of that of the other motors; therefore, the angular momentum of the ball, which can affect the trajectory of the ball, can be controlled by the launching means. More preferably and optionally, the launching means comprises two wheels, and even more preferably, they comprise two electric launching motors, each of which is connected to a corresponding wheel and configured to control the movement of said wheel.

To be able to control the trajectory of the ball more precisely when it is launched, the system optionally comprises first directional control means, which are configured to control a horizontal direction in which the ball is launched. Optionally and preferably, said first directional control means are configured to rotate the outlet chamber and/or the launching means and/or the outlet mouth with respect to a first axis of rotation, wherein the first axis of rotation is perpendicular and/or not parallel to the surface of the playing field; thus, the horizontal direction in which the ball is launched can be controlled. Optionally and preferably, the first directional control means are configured to rotate the outlet chamber and/or the launching means about a vertical axis and in this case, it is preferred that the system has an optional additional feature which is that the longitudinal direction of the outlet conduit is also vertical. The first directional control means can, for example, comprise a first rotating gear system and comprise a first directional control electric motor that is optionally connected to the outlet chamber and/or below, inside or to the side of the outlet chamber. Preferably, the first directional control electric motor is connected to the first rotating gear system and also configured to surround the latter, which can be connected to the outlet conduit and configured to rotate the outlet chamber with respect to the outlet conduit. Optionally and preferably, the first directional control means are configured to rotate the launching means and/or the outlet chamber and/or a portion of the outlet chamber when the outlet chamber is in any position, for example, when it is in the first position and/or second position.

To be able to control the trajectory of the ball that is launched by the system more precisely, the latter optionally comprises second directional control means, which are configured to control a non-horizontal direction in which the ball is launched. Optionally and preferably, said second directional control means are configured to rotate the outlet chamber and/or the launching means about a second axis of rotation, wherein the second axis of rotation is parallel and/or not vertical to the surface of the playing field; thus, the non-horizontal direction in which the ball is launched is controlled. Optionally and preferably, the second directional control means are configured to rotate the outlet chamber and/or the launching means about a horizontal axis, and in this case the longitudinal direction of the outlet conduit is optionally and preferably vertical. For example, the second directional control means are optionally configured to rotate the wheels of the launching means about a geometric axis that is parallel to the plane of the wheel disc, when the launching means comprise said wheels as mentioned in the variations described above. The second directional control means can, for example, comprise a second rotating gear system and/or a second rotation transmission system and comprise a second directional control electric motor that is optionally situated on or inside the outlet chamber. In this case, the second directional control electric motor is preferably connected to the second rotating gear system or to the second rotation transmission system, and it is also configured to surround the latter, which is optionally connected to the launching means and configured to rotate them. Optionally and preferably, the second directional control means are configured to rotate the launching means and/or the outlet chamber when the latter is in any position, for example, when it is in the first position or second position.

It is envisaged that optionally the system further comprises recording means that are configured to detect and record the presence of the ball in the system. The recording means optionally, and as a non-limiting example, comprise a photocell and/or a motion detector and/or a pressure sensor arranged at any point in the system through which the ball can pass, and they are configured to detect the presence or passing of the ball and transmit a corresponding detection signal which is preferably an electrical signal. By being able to detect and record the presence of the ball, the system offers the advantage of being able to notify the user when the system is completely ready to be used, i.e., when the system contains the ball. This can prevent the system from being used incorrectly, which could impede the match.

Optionally, the system further comprises system control means configured to control the system automatically and/or under the manual intervention of a user. Said control means optionally and preferably comprises a general control CPU. The control means are optionally connected to any electrical or electromechanical element of the system, and for example, to the launching means, and/or to the first and/or second directional control means, and/or to the movement means and/or to the recording means, the control means being configured to control any of the mentioned elements or others.

The system of the first aspect of the present invention is suitable for use on football fields since it offers all the functionalities and advantages that are required by the systems to be used in this sport. For this reason, and in relation to said first aspect of the invention, the playing field is optionally a football field, the ball is a football, and the ground comprises natural and/or artificial grass.

Optionally, the system of the first aspect of the invention comprises transportation means arranged under the ground, wherein said transportation means comprise a first end and a second end which is connected to the outlet conduit, and wherein the transportation means are configured to: receive the ball at the first end; direct said ball from said first end to the second end; pass said ball from the second end into the outlet chamber when the latter is in the first position. Indeed, incorporating the transportation means into the system offers the additional advantage that the ball can be introduced into the system from a point that is substantially outside the area where the players play. In a non-limiting example, the transportation means comprise a simple conduit in which the ball fits and can pass from the first end of the simple conduit to the second end of the simple conduit, wherein said first end and said second end are respectively the first end and the second end of the transportation means. In a preferred variation of the last example, the simple conduit is parallel or inclined with respect to the level of the upper surface of the ground of the playing field, and the second end of the simple conduit is a mouth which is opposite the outlet chamber and/or the outlet mouth when the outlet chamber is in the first position. When the simple duct is inclined as mentioned above, the second end is preferably lower than the first end. Optionally, the system comprises ball introduction means, which are configured to receive the ball when the latter is introduced into the system. Said ball introduction means are optionally connected to the first end of the transportation means when the latter are comprised in the system. In a non-limiting example, the ball introduction means comprise an introduction conduit that optionally protrudes from the ground at a point on the ground that is optionally outside the area of the ground where the match is played, and said introduction conduit is partially inserted in the ground and connected to the transportation means and configured to pass the ball that is introduced into the system to the latter.

In the case where the system comprises the transportation means mentioned above, the second end of the transportation means optionally comprises a stay chamber configured to contain the ball before the ball passes to be received by the outlet chamber. By using the stay chamber, the ball is positioned in a position that is suitable for the ball to quickly enter the outlet chamber without error when the latter is in the second position. This improves the reliability of the system. Likewise, it is envisaged that the system, and for example the optional transportation means mentioned above, can contain a plurality of balls at any time; in this case and when the system comprises the stay chamber, the latter can allow one single ball to enter the outlet chamber at a time when the latter is in the first position.

In the case that the system comprises the transportation means mentioned above, the second end of the transportation means optionally comprises a ball lifting mechanism arranged just before the outlet conduit and configured to collect and lift the ball to a position that allows the ball to enter the outlet chamber when the latter is in the first position thereof. In the case that, for example, the second end of the transportation means comprises the stay chamber mentioned above, said stay chamber can comprise said lifting mechanism. The lifting mechanism can optionally comprise a platform that receives the ball and an electric motor that connects to the platform; therefore, it is understood that the lifting mechanism can take the form of a mini-lift. The lifting mechanism preferably lifts the ball to a position where the ball is opposite the outlet chamber so that the ball can be introduced into the outlet chamber by preferably and optionally passing through the outlet mouth. It is important to note that the outlet chamber is optionally configured so that the ball can enter the outlet chamber when the latter is in the first position. Likewise, the outlet chamber optionally comprises an inlet mouth through which the ball can enter the outlet chamber when the latter is in the first position. Likewise, the outlet chamber optionally comprises closing means, which for example comprise a door and which are configured to close the outlet mouth and/or the optional inlet mouth, said closing means thus protecting the inside of the outlet chamber against adverse factors.

In the case in which the system comprises the transportation means mentioned above, the optional variation of the system is envisaged, wherein the ground comprises a first portion and a second portion separated from each other by lines formed on the ground and/or barriers that are on the ground, and wherein the first end is in the first portion of the ground and the second position of the outlet chamber is on the second portion of the ground. In the optional case where the playing field is a football field, the second portion is the area with grass where players on the football team usually play and/or run when they go after and touch the ball during the football match; and the first portion is the area around the grass, and the lines formed on the ground are the white lines of the field that define the various edges related to the rules of the sport, such as the baseline, and the barriers can be or can comprise billboards for example. When the first end is in the first portion, it ensures that the introduction of a ball into the first end does not present any danger to the players and said introduction cannot impede the match. In this case, the system optionally comprises the ball introduction means mentioned above.

Optionally, the system comprises a cover that can be connected to the upper end of the outlet conduit through which the outlet chamber passes when the latter moves between the first position and the second position. Preferably, the cover is configured to move by covering and uncovering said end, respectively allowing and not allowing the outlet chamber to move towards the second position. Preferably, the cover is configured so that it is level with the ground surface of the playing field where the players play, when said cover is covering said end.

The outlet chamber can comprise an inlet mouth (opening). The inlet mouth can be situated on an upper surface of the outlet chamber. The outlet chamber can comprise a door/cover, for example an upper door/cover, configured to close said inlet mouth. The latter can be used to easily insert the ball into the outlet chamber, preferably when said outlet chamber is in the first position. More preferably, the first position is below the ground, for example when the system is installed. The system can comprise a spiral-shaped ramp (track, tube). Optionally, the ramp can have a first portion and a second portion. Preferably, the second portion can be lower than the first portion, for example when the system is installed on the playing field. Optionally, a ball after being introduced into the outlet chamber, for example when the system is in the first position, can pass, or fall by gravity, through the outlet mouth and enter said optional ramp. The possibility that the ball can enter said optional first portion of the ramp is envisaged. In a non-limiting example, due to the effect of gravity, the ball can move down said optional ramp, passing through the second optional portion of the ramp. Said second portion can be a tunnel or tube through which the ball passes.

Likewise, the system can optionally comprise an apparatus (device, subsystem) that provides ozone and/or ultraviolet light in the ramp through which the ball passes. Preferably, said system provides ozone, for example by means of oxygen in the air. Said apparatus is preferably connected to the second portion. Optionally, the system is configured so that ozone and/or ultraviolet light is provided by said optional apparatus in an area through which the ball passes; this area is preferably the aforementioned optional second portion of said ramp. It is envisaged that the ozone effect and/or ultraviolet light can at least partially disinfect the surface of the ball. This ensures that players have less risk of being infected by some microorganisms, for example viruses such as SARS-COV-2 or bacteria, which can stick to the ball before or during the match. The system can optionally further comprise a provider mechanism for providing/introducing (or reintroducing) the ball into the outlet chamber. Said optional provider mechanism can preferably have a movable part, which can also be considered a collector, configured to collect the ball when for example it exits said optional second portion of the optional ramp. Said optional movable part (collector) can provide the ball in the outlet chamber, preferably by means of an optional providing door or mouth that can be optionally situated below the outlet chamber. In the system, the outlet chamber can move between the first position and the second position by means of the movement means that optionally comprise two actuators; the latter can optionally be pneumatic, electric or hydraulic actuators. Preferably, the outlet chamber moves between the first position and the second position, passing through an outlet conduit which can optionally be or comprise a perimeter frame or structure. Said perimeter structure (frame) preferably comprises an upper mouth which preferably has a ring shape. Preferably, the outlet chamber moves between the first position and the second position in an arc-shaped motion. Preferably, the launching means comprise two wheels. Optionally, the system comprises first directional control means which are configured to control a horizontal direction in which the ball is launched. Optionally, said optional first directional control means move a structure, for example, the aforementioned optional perimeter structure, which preferably supports the outlet chamber. Said optional structure or perimeter structure is preferably rigid.

Optionally, the system further comprises a measuring apparatus configured to measure, or evaluate, the pressure of the ball. Optionally and preferably, said measuring apparatus is connected to said optional ramp, more preferably at the end of the optional second part of said ramp described above. Optionally, the pressure of the ball in the system is measured when the latter exits an area in which it is optionally disinfected. Likewise, said optional measuring apparatus comprises a pressure cylinder for applying pressure on the ball in order to evaluate the pressure of the ball. When the pressure of the ball is not suitable or not in accordance with the rules of the sport, the ball can be discarded and/or not used by the players The present invention in its second aspect is a playing field that comprises a system for launching balls onto the ground of the playing field, wherein the system is a system according to the first aspect of the invention and according to any of the examples or versions or embodiments of said system mentioned above.

To solve the same technical problem that is solved by the system of the first aspect of the invention, the present invention in a third aspect is a method for launching a ball onto the ground of a playing field, wherein the method comprises:

positioning in a first position that is under the ground an outlet chamber comprising an outlet mouth and launching means for launching the ball arranged in said outlet chamber and configured to apply pressure on the ball forcing it to exit the outlet chamber and enter onto the ground through the outlet mouth, the outlet chamber being configured to receive the ball therein when the outlet chamber is in said first position, and the outlet chamber being contained in an outlet conduit that is configured to contain the outlet chamber and allow the latter to move through the outlet conduit to a second position that is on the ground and in which the ball can exit from the outlet chamber to the ground;

introducing the ball into the outlet chamber;

moving the outlet chamber to a second position using movement means connected to and configured to move said outlet chamber between at least the first position and the second position;

using the launching means to apply pressure on the ball forcing it to exit the outlet chamber and enter onto the ground through the outlet mouth.

The method of the third aspect of the invention relates to the use of the system according to the first aspect of the invention and any embodiment of said system. The actions that are part of the method of the third aspect of the invention offer the same advantages and technical solutions that are described above in relation to the system of the first aspect of the invention. It is worth noting that any action described above in relation to the use and/or operation of the various essential or optional technical components and limitations of the system can be comprised by the method of the third aspect of the invention as an element of said method.

DETAILED DESCRIPTION OF THE EMBODIMENTS

Figure 1:
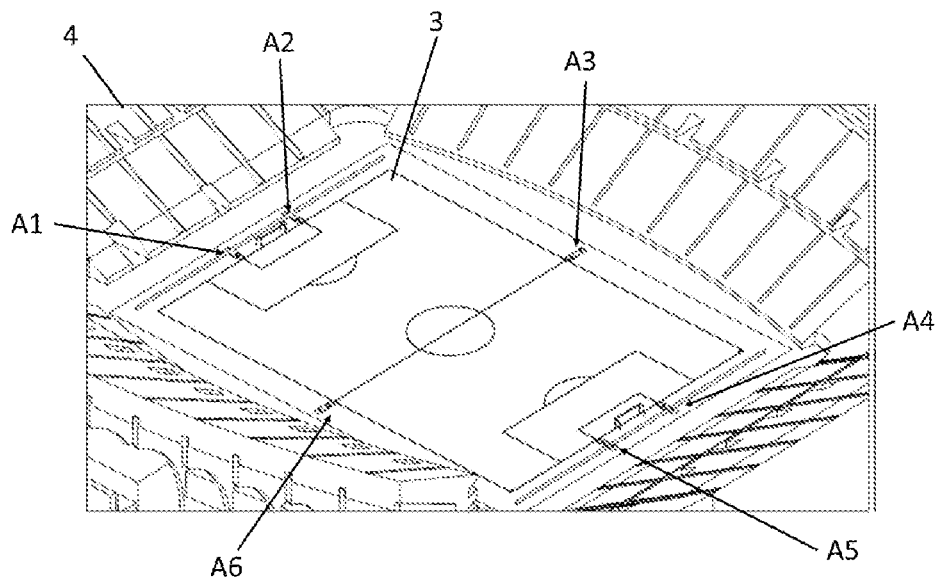
FIG. 1 shows the ground of a playing field according to the second aspect of the invention, wherein the sport is football and the playing field comprises a system according to the first aspect of the invention.

The playing field 4 shown in FIG. 1 comprises a system for launching balls onto the ground 3 of a playing field, wherein the system is a preferred embodiment according to the first aspect of the invention. The playing field 3 in FIG. 1 is a preferred embodiment of the second aspect of the invention; in this embodiment, the playing field comprises six ball launching systems, which are located approximately in the corresponding positions A1, A2, A3, A4, A5 and A6 shown in FIG. 1.

Figure 2:
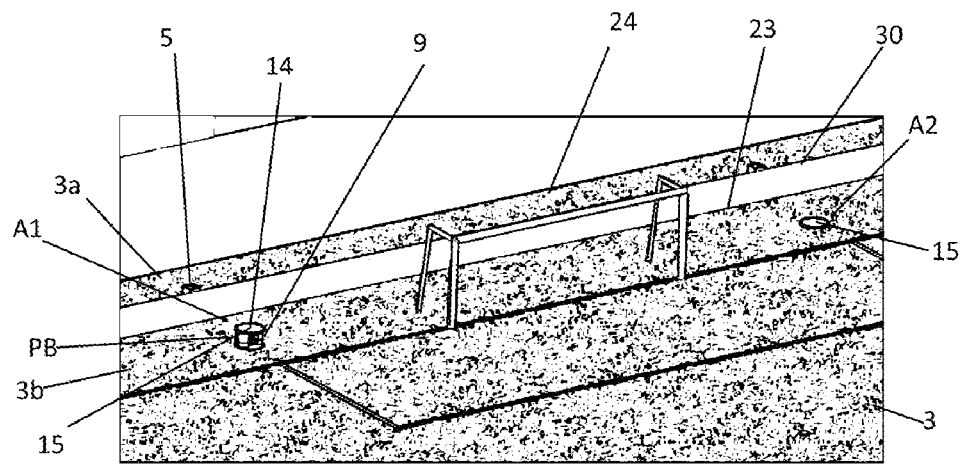
FIG. 2 shows a portion of the playing field of FIG. 1.

A specific portion of the playing field 4 and the ground 3 thereof which includes the systems arranged in positions A1 and A2 and also includes the post that is situated near the two systems is shown in FIG. 2, wherein the surface of the ground 3 of the playing field comprises grass which is shown by the texture drawn in FIG. 2. Each of the systems in A1 and A2 is a system according to a preferred embodiment of the system of the first aspect of the invention. FIG. 2 shows that the system arranged in A1 comprises an outlet chamber 9, which is in the second position PB that is on the ground 3 and wherein the ball can exit from the outlet chamber 9 to the ground 3. The system that is arranged in A1 also comprises ball introduction means 5, which are configured to receive the ball when the latter is introduced into the system; the system comprises transportation means which are not shown in FIG. 2. The ball introduction means 5 are connected to a first end (not shown in FIG. 2) of said transportation means. In each of the systems in A1 and A2, the outlet chamber 9 comprises a finishing part 14 that forms the upper stop of the outlet chamber 9 and has an upper surface 15 which is configured to have a similar texture and be level with the ground 3 that surrounds and limits said upper surface 15 when the rest of the outlet chamber is under the ground. In this case, the similar texture is the grass texture. In the system in A2, the outlet chamber (not shown) comprises a finishing part (not shown) that forms the upper stop of the outlet chamber and has an upper surface 15 which has a texture similar to that of the ground 3 that surrounds and limits said upper surface 15; likewise, in the snapshot shown in FIG. 2, the rest of the outlet chamber of the system in A2 is under the ground and the upper surface 15 of the same system is level with the ground 3 that surrounds and limits said upper surface 15. Likewise, as mentioned above, it is understood that FIG. 2 shows that the ground 3 comprises a first portion 3a and a second portion 3b separated from each other by lines 23, 24 formed on the ground and barriers 30 that are on the ground 3, and wherein the first end (not shown) of the transportation means (not shown), which is vertically under the ball introduction means 5, is in the first portion 3a of the ground; likewise, the second position PB of the outlet chamber 9 is on the second portion 3b of the ground 3.

Figure 3:
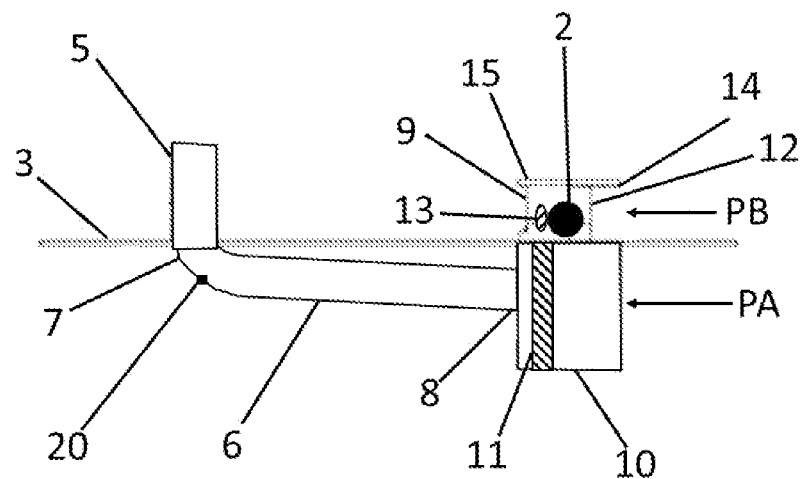
FIG. 3 is a diagram showing an embodiment of the system of the first aspect of the invention, wherein the system is arranged on the ground of a playing field. The plane of the diagram is vertical to the plane of the ground.

A cross section of an embodiment of the system according to the first aspect of the invention is shown in FIG. 3. Specifically, FIG. 3 shows a system for launching a ball onto the ground 3 of a playing field, wherein the system comprises:

An outlet chamber 9 that is configured to receive the ball 2 therein when the outlet chamber 9 is in a first position PA that is under the ground 3;

An outlet conduit 10 that is configured to contain the outlet chamber 9 and allow the latter to move through the outlet conduit 10 towards a second position PB that is on the ground 3 and in which the ball 2 can exit from the outlet chamber 9 to the ground 3;

Movement means 11 of the outlet chamber 9, connected to and configured to move said outlet chamber 9 between at least the first position PA and the second position PB, Wherein the outlet chamber 9 comprises an outlet mouth 12 and launching means 13 for launching the ball 2 arranged in said outlet chamber 9 and configured to apply pressure on the ball 2 forcing it to exit the outlet chamber 9 and enter onto the ground 3 through the outlet mouth 12.

FIG. 3 also shows that the system further comprises transportation means 6 arranged under the ground 3, wherein said transportation means 6 comprise a first end 7 and a second end 8 which is connected to the outlet conduit 10, and wherein the transportation means 6 are configured to: receive the ball 2 at the first end 7; direct said ball 2 from said first end 7 to the second end 8; pass said ball 2 from the second end 8 into the outlet chamber 9 when the latter is in the first position PA.

Likewise, the system of the embodiment shown in FIG. 3 further comprises recording means 20 that are configured to detect and record the presence of the ball 2 in the system; in the embodiment shown, the recording means 20 comprise a pressure sensor which is activated by the weight of a ball passing over the sensor by pressing it.

Figure 4:
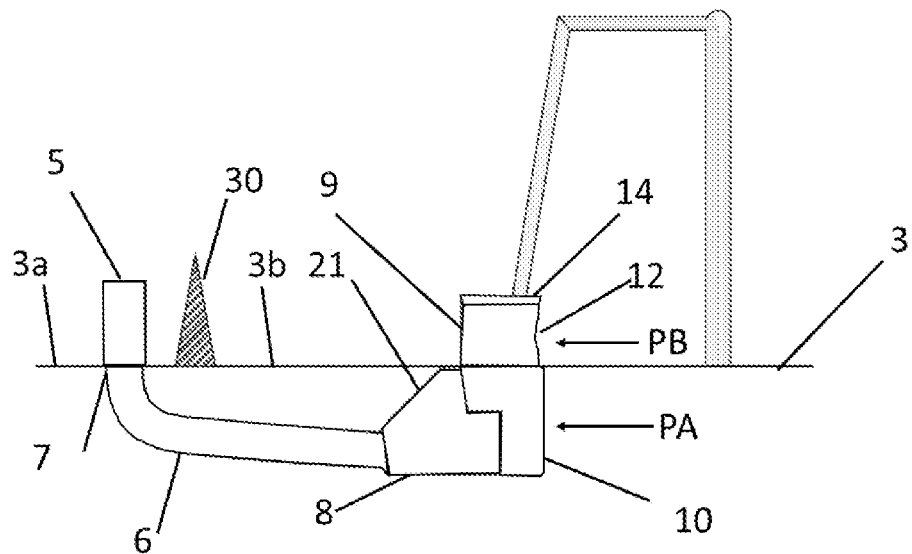
FIG. 4 is a side elevation view of a preferred embodiment of the system of the first aspect of the invention, wherein the system is arranged near a post in the ground of a playing field.

Another embodiment of the system of the first aspect of the invention is shown in FIG. 4. Similar to the system shown in FIG. 3, the preferred embodiment of the system shown in FIG. 4 comprises transportation means 6 arranged under the ground 3, wherein said transportation means 6 comprise a first end 7 and a second end 8 which is connected to the outlet conduit 10, and the transportation means 6 are configured to: receive the ball (not shown) at the first end 7; direct said ball 2 from said first end 7 to the second end 8; pass said ball from the second end 8 into the outlet chamber 9 when the latter is in the first position PA. Likewise, the system in FIG. 4 comprises ball introduction means 5, which are connected to the first end 7. Likewise, FIG. 4 shows that the ground 3 comprises a first portion 3*a* and a second portion 3*b* separated from each other by barriers 30 that are on the ground 3, and the first end 7 is in the first portion 3*a* of the ground and the second position PB of the outlet chamber 9 is on the second portion 3*b* of the ground 3. The barriers 30 shown are billboards. Likewise, in the system shown in FIG. 4, the second end 8 of the transportation means comprises a stay chamber 21 configured to contain the ball before the ball is received by the outlet chamber 9. The system shown in FIG. 4 is arranged on a football field in such a way that when the outlet chamber 9 is in the second position PB, said chamber is situated 8 metres, and more preferably 4 metres, from the post shown which is the closest post, such that the ball is easily and precisely introduced onto the ground towards the goalkeeper during the football match.

Figure 5:
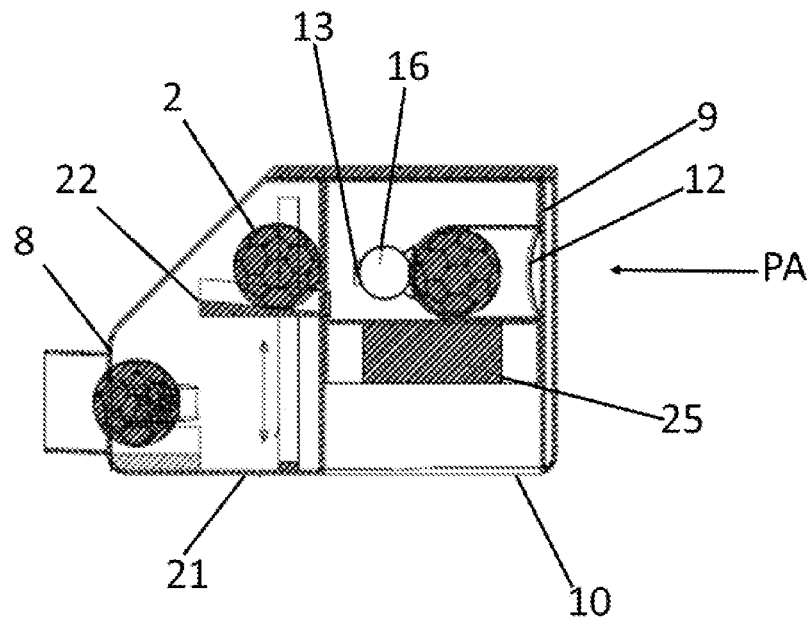
FIG. 5 shows a cross section of a portion of one embodiment of the system.

In FIG. 5, a cross section of an embodiment of the system is shown, wherein the system is a system according to the embodiment shown in FIG. 3, with the difference that the outlet chamber 9 of the system in FIG. 5 is in the first position PA. The plane of FIG. 5 is parallel to the direction of movement of the outlet chamber 9 from the first position PA to the second position (not shown), and it is perpendicular to the surface of the ground where the system is installed. Likewise, FIG. 5 shows three balls which are in various positions in the system. FIG. 5 is understood to show that the second end 8 of the transportation means comprises a ball lifting mechanism 22 arranged just before the outlet conduit 10 and configured to collect and lift the ball 2 to a position that allows the ball 2 to enter the outlet chamber 9 when the latter is in the first position PA thereof. In the specific embodiment described in FIG. 5, the lifting mechanism is inside the stay chamber 21. Likewise, in the embodiment shown in FIG. 5, the launching means 13 comprise a pneumatic system 16 that is configured to provide pressurised air or gas in the outlet chamber 9 to launch the ball 2. In this specific case, the pneumatic system comprises at least one nozzle that is arranged in a position inside the chamber, and this position is substantially behind the outlet mouth and the ball which is situated between the outlet mouth and the nozzle when the ball is in the outlet chamber and properly positioned to be launched by the system.

Likewise, the system shown in FIG. 5 comprises first directional control means 25, which are configured to control a horizontal direction in which the ball 2 is launched. In the specific embodiment shown in FIG. 5, the first directional control means 25 are configured to rotate the outlet chamber with respect to a first axis of rotation which is vertical and, likewise, the first directional control means 25 comprise a first directional control electric motor that is connected to the outlet chamber 9. In this case, the first directional control electric motor can rotate the outlet chamber with respect to the outlet conduit 10, when the outlet chamber 9 is in the second position or in the first position PB.

Figure 6:
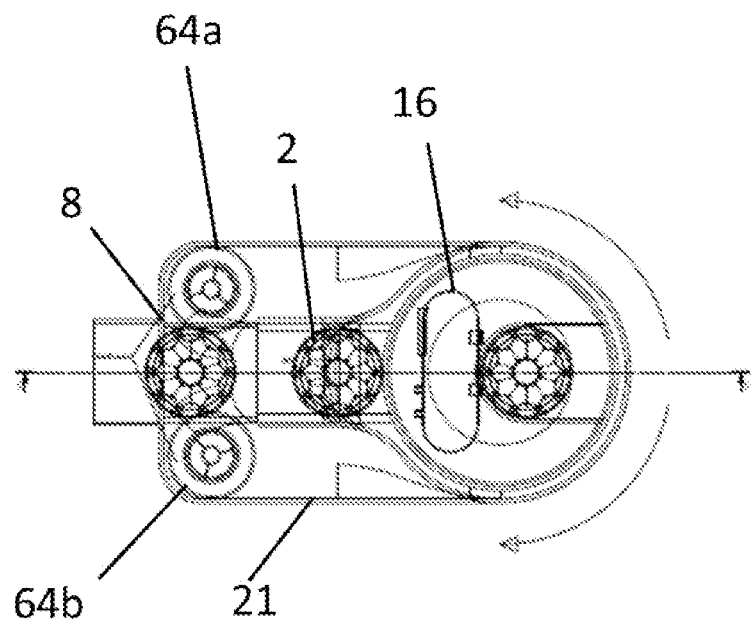
FIG. 6 shows another cross section of the portion of the embodiment of the system shown in FIG. 5.

A different view of the system of the embodiment of FIG. 5 is shown in FIG. 6. The plane of FIG. 6 is perpendicular to the direction of movement of the outlet chamber from the first position (not shown) to the second position (not shown), and it is parallel to the surface of the ground where the system is installed. FIG. 6 shows with curved arrows the directions in which the first rotation means shown in FIG. 5 can rotate the outlet chamber. Likewise, FIG. 6 shows that the transportation means, which comprise the second end 8, comprise a pair of wheels 64*a*, 64*b* which are configured to hold the ball 2 and surround it, thus moving the ball towards the outlet conduit and the outlet chamber.

Figure 7:
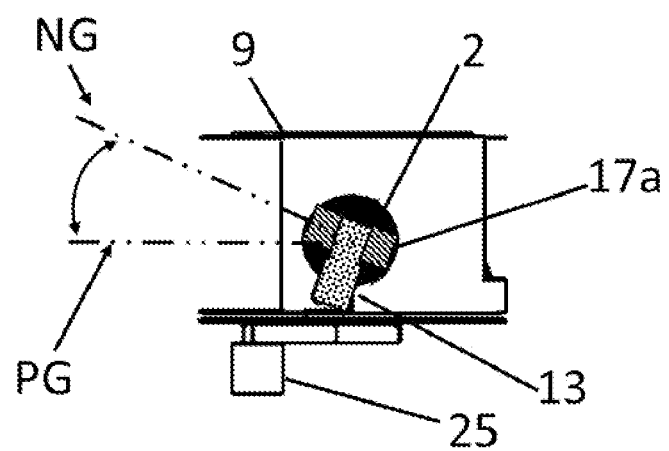
FIG. 7 is a view of a portion of one embodiment of the system.

FIG. 7 is a view of a portion of an embodiment of the system, said portion including the outlet chamber 9, and FIG. 7 does not show the outer walls of the outlet chamber which prevent observing the shown components that the chamber comprises therein. FIG. 7 shows that the outlet chamber comprises launching means 13 therein. Likewise, in the embodiment shown in FIG. 7, the system comprises first directional control means 25, which are configured to control a horizontal direction in which the ball 2 is launched. The horizontal direction belongs to the same plane as the horizontal axis PG, which in this case is parallel to the upper surface of the ground of the field. In FIG. 7, the first directional control means 25 comprise an electric motor which is connected to the chamber and configured to rotate the chamber about an axis (not shown) which is parallel to the plane of FIG. 7 and perpendicular to the surface of the ground and the horizontal axis PG. FIG. 7 shows that the launching means 13 comprise a wheel 17*a* which, when rotated, propels the ball 2 so that the latter is launched in the horizontal direction or in the non-horizontal direction which is shown by the non-horizontal axis NG.

Figure 8:
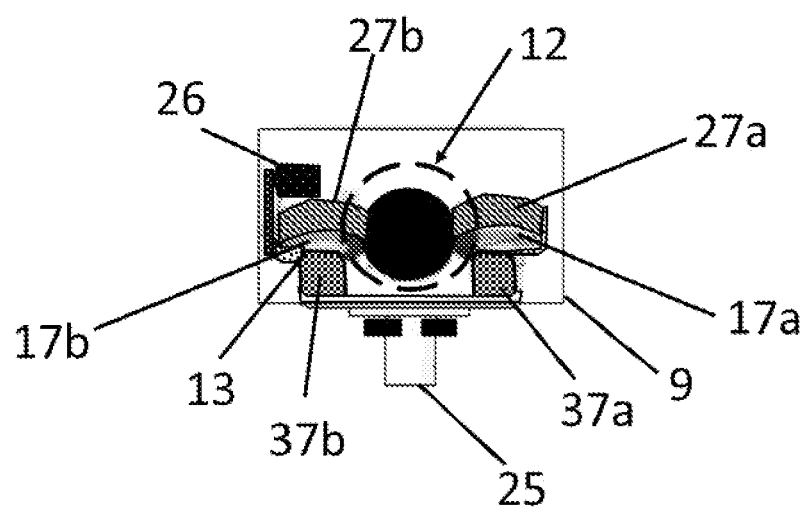
FIG. 8 is a different view of the same portion of the embodiment of the system shown in FIG. 7.

FIG. 8 is a different perspective of the portion of the same embodiment of the system shown in FIG. 7, and the plane of FIG. 8 is perpendicular to the parallel axis PG shown in FIG. 7. FIG. 8 does not show the outer walls of the outlet chamber, which prevent observing the shown components that the chamber comprises therein, and it shows, by means of a dashed circle, the shape of the outlet mouth 12 which is comprised by the outlet chamber 9. Likewise, FIG. 8 shows that the launching means 13 comprise two wheels 17*a*, 17*b* that can rotate and each one comprises an edge 27*a*, 27*b*, and at least said two wheels 17*a*, 17*b* are configured so that the ball 2 is inserted therebetween and contacted by said edges 27*a*, 27*b*, i.e., the ball is in contact with said edges, and they are configured to launch the ball when they rotate by propelling the ball by rotating said edges 27*a*, 27*b*. When the ball is launched, it passes through the outlet mouth 12. In this specific embodiment, the launching means 13 comprise two electric launching motors 37a, 37b, each being connected to the corresponding wheel 17a, 17b and configured to rotate it when activated so that the ball is launched. Likewise, in the embodiment shown in FIG. 8, the system comprises second directional control means 26, which are configured to control a non-horizontal direction in which the ball 2 is launched. The non-horizontal direction is parallel to the non-horizontal axis NG shown in FIG. 7, and the non-horizontal axis NG can move with respect to the horizontal axis PG in the directions shown by the curved geothermal line and ending in the two arrows shown in FIG. 7. In the embodiment shown in FIG. 7 and FIG. 8, the second directional control means 26 comprise a second rotation transmission system and a second electric motor which is connected to the launching means by means of the second rotation transmission system.

Figure 9:
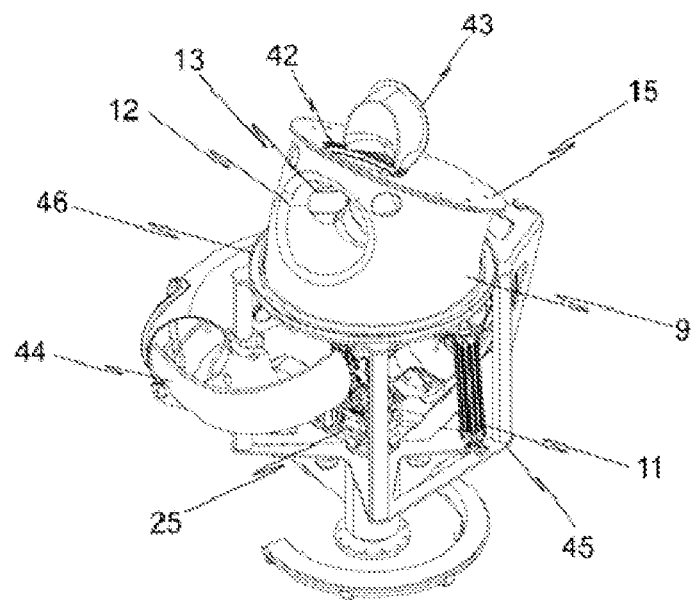
FIG. 9 is a view of another preferred embodiment of the system of the first aspect of the invention, which comprises a subsystem for disinfecting the ball.
Figure 10:
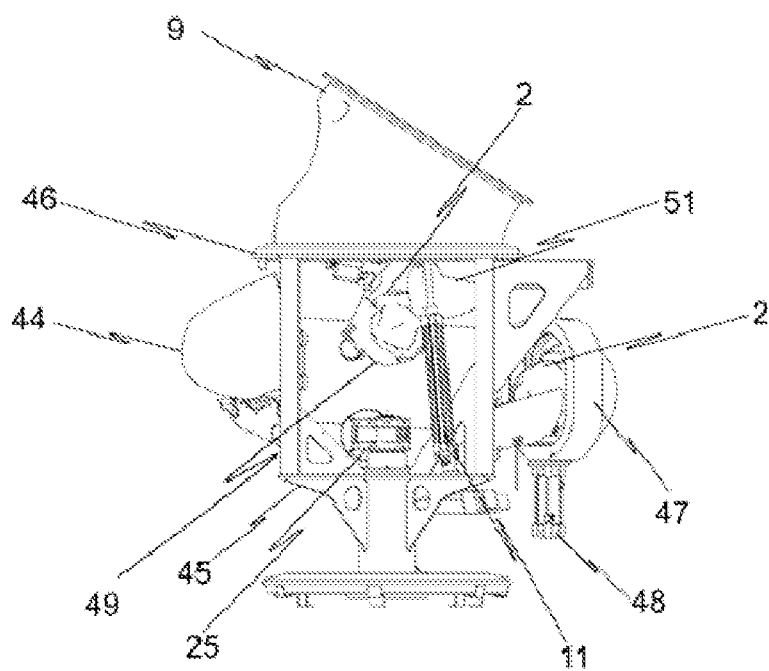
FIG. 10 is a side view of the embodiment shown in FIG. 9.
Figure 11:
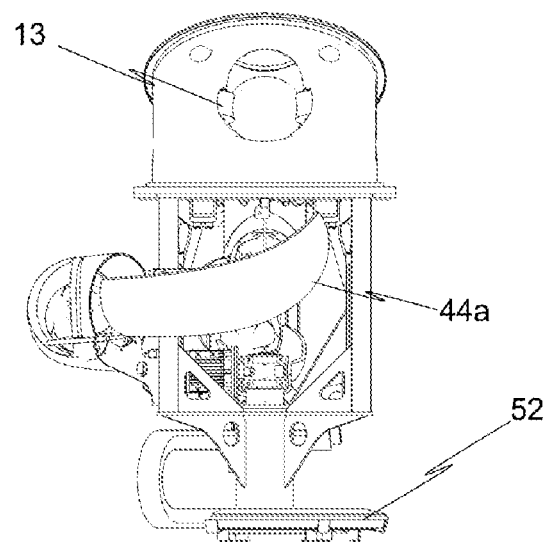
FIG. 11 is a front view of the embodiment shown in FIG. 9.
Figure 12:
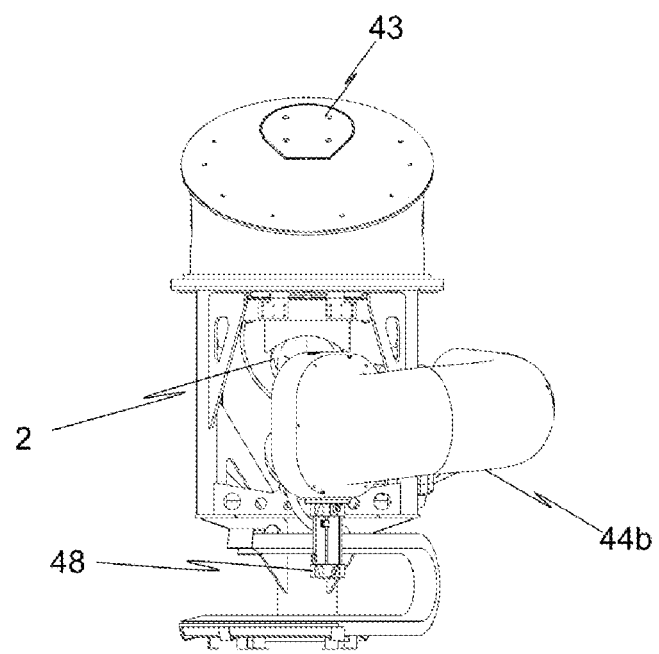
FIG. 12 is a rear view of the embodiment shown in FIG. 9.

FIGS. 9-12 show another preferred embodiment of the system according to the first aspect of the invention. FIGS. 9-12 show the system when the outlet chamber 9 of the system is in the second position thereof. When the system is installed on a playing field, the second position is on the ground (not shown). In said other preferred embodiment, the outlet chamber 9 comprises an inlet mouth (opening) 42 which is on the upper surface 15 of the outlet chamber 9. The latter comprises an upper door/cover 43 configured to close said inlet mouth 42 which can be used to easily insert the ball into the outlet chamber, especially when said outlet chamber is in the first position (not shown in FIG. 9-12). The first position is below the ground when the system is installed. The system in FIG. 9 comprises a spiral-shaped ramp 44 (track, tube). The ramp has a first portion 44a and a second portion 44b. When the system is installed on the playing field, the second portion 44b is lower than the first portion 44a. When the system is in the first position, a ball 2 that is in the outlet chamber can pass, or fall by gravity, through the outlet mouth 12 and enter the first portion 44a of the ramp. Due to the effect of gravity, the ball moves down the ramp, passing through the second portion 44b of the ramp. The second portion 44b is a tunnel/tube through which the ball passes. The system of FIG. 10 comprises an apparatus (device) (not shown in FIG. 10) that provides ozone and/or ultraviolet light in the ramp through which the ball passes. In the embodiment shown, said apparatus is connected to the second portion 44b, and the system is configured so that ozone and/or ultraviolet light is provided in an area through which the ball passes; said area in this embodiment is the second portion 44b. It is envisaged that ozone and/or ultraviolet light can at least partially disinfect the surface of the ball. The embodiment shown in FIG. 10 and FIG. 12 further comprises a measuring apparatus 48 configured to measure, or at least evaluate, the pressure of the ball. In the embodiment shown, said measuring apparatus 48 is connected to, and at the end of, the second portion 44b to measure the pressure of the ball when the latter exits the area where it is disinfected. Likewise, in the embodiment shown, said measuring apparatus comprises a pressure cylinder for applying pressure on the ball in order to evaluate the pressure of the ball. When the pressure of the ball is not suitable or not in accordance with the rules of the sport, the ball can be discarded and/or not used by the players. The system further comprises a provider mechanism 49 for providing/introducing (or reintroducing) the ball into the outlet chamber 9. In the embodiment shown, the provider mechanism 49 has a movable part, which can also be considered a collector, configured to collect the ball that exits the second portion 44b of the ramp. Said movable part (collector) passes the ball into the outlet chamber through a providing door or mouth (not shown) that is below the outlet chamber. In the system shown, the outlet chamber moves between the first position and the second position by the action of the movement means 11, which in this specific case comprise two actuators (FIGS. 9-10 show one of the actuators), which can be pneumatic, electric or hydraulic actuators. The outlet chamber moves between the first position and the second position, passing through an outlet conduit 10 which in the embodiment shown in FIGS. 9-12 is a perimeter structure or frame 45 comprising a ring-shaped mouth 46. In the embodiment shown, the outlet chamber moves between the first position and the second position in an arc-shaped motion. In the system of FIGS. 9-12, the launching means 13 comprises two wheels (rollers). Likewise, it is shown in FIG. 9 that the system comprises first directional control means 25, which are configured to control a horizontal direction in which the ball (2) is launched.

With regards to the preferred embodiment described above, the following method is described:
   Letting a ball pass through an area where ozone and/or ultraviolet light is provided
   Providing (introducing) the ball into the outlet chamber
   Moving the outlet chamber from the first position thereof to the second position thereof
   Launching the ball from the outlet chamber to the surface of the ground using launching means situated inside the outlet chamber.

A preferred embodiment of the method according to the third aspect of the invention is a method for launching a ball onto the ground of a playing field, wherein the method comprises:
   positioning in a first position that is under the ground an outlet chamber comprising an outlet mouth and launching means for launching the ball arranged in said outlet chamber and configured to apply pressure on the ball forcing it to exit the outlet chamber and enter onto the ground through the outlet mouth, the outlet chamber being configured to receive the ball therein when the outlet chamber is in said first position, and the outlet chamber being contained in an outlet conduit that is configured to contain the outlet chamber and allow the latter to move through the outlet conduit to a second position that is on the ground and in which the ball can exit from the outlet chamber to the ground;
   introducing the ball into the outlet chamber;
   moving the outlet chamber to a second position using movement means connected to and configured to move said outlet chamber between at least the first position and the second position;
   using the launching means to apply pressure on the ball forcing it to exit the outlet chamber and enter onto the ground through the outlet mouth.

In one embodiment, the method comprises applying ozone and/or ultraviolet light to the surface of the ball.

The foregoing embodiment of the method can be performed using any of the embodiments of the system of the first aspect of the invention described above.

Having sufficiently described the nature of the invention, in addition to a preferred exemplary embodiment, it is hereby stated for the relevant purposes that the materials, shape, size and layout of the described elements may be modified, provided that it does not imply altering the essential features of the invention claimed below.

The invention claimed is:

1. A system for launching a ball onto the ground of a playing field, wherein the system comprises:
   an outlet chamber that is configured to receive the ball therein when the outlet chamber is in a first position that is under the ground;
   an outlet conduit or frame that is configured to contain the outlet chamber and allow the same to move through the outlet conduit or frame towards a second position that is on the ground and in which the ball can exit from the outlet chamber to the ground; and
   movement means of the outlet chamber connected to and configured to move said outlet chamber between at least the first position and the second position,
   wherein the outlet chamber comprises an outlet mouth and launching means for launching the ball arranged in said outlet chamber and configured to apply pressure on the ball forcing it to exit the outlet chamber and enter onto the ground through the outlet mouth.

2. The system according to claim 1, wherein the outlet chamber comprises a finishing part that forms the upper stop of the outlet chamber and has an upper surface which is configured to have a similar texture and be level with the ground that surrounds and limits said upper surface when the rest of the outlet chamber is under the ground.

3. The system according to claim 1, wherein the launching means comprise a pneumatic system that is configured to provide pressurized air or gas in the outlet chamber to launch the ball.

4. The system according to claim 1, wherein the launching means comprise at least two wheels that can rotate and each one comprises an edge, and wherein said wheels are configured so that the ball is inserted therebetween and contacted by said edges, and they are configured to launch the ball when they rotate, propelling the ball by rotating said edges.

5. The system according to claim 1, wherein the system comprises first directional control means, which are configured to control a horizontal direction in which the ball is launched.

6. The system according to claim 1, wherein the system comprises second directional control means, which are configured to control a non-horizontal direction in which the ball is launched.

7. The system according to claim 1, wherein the system further comprises recording means that are configured to detect and record the presence of the ball in the system.

8. The system according to claim 1, which further comprises transportation means arranged under the ground, wherein said transportation means comprise a first end and a second end which is connected to the outlet conduit or frame, and wherein the transportation means are configured to: receive the ball at the first end ; direct said ball from said first end to the second end; pass said ball from the second end into the outlet chamber when the latter is in the first position.

9. The system according to claim 8, wherein the second end of the transportation means comprises a stay chamber configured to contain the ball before the ball is received by the outlet chamber.

10. The system according to claim 8, wherein the second end of the transportation means comprises a ball lifting mechanism arranged just before the outlet conduit or frame and configured to collect and lift the ball to a position that allows the ball to enter the outlet chamber when the latter is in the first position thereof.

11. The system according to claim 1, further comprising an apparatus that is configured to provide ozone and/or ultraviolet light in an area of the system.

12. The system according to claim 1, wherein the outlet conduit or frame comprises a structure.

13. The system according to claim 1 further comprising a provider mechanism configured to provide the ball in the outlet chamber.

14. The system according to claim 1, further comprising a measuring apparatus configured to measure the pressure of the ball.

15. A method for launching a ball onto the ground a playing field, wherein the method comprising:
   positioning in a first position that is under the ground an outlet chamber comprising an outlet mouth and launching means for launching the ball arranged in said outlet chamber and configured to apply pressure on the ball forcing it to exit the outlet chamber and enter onto the ground through the outlet mouth, the outlet chamber being configured to receive the ball therein when the outlet chamber is in said first position, and the outlet chamber being contained in an outlet conduit or frame that is configured to contain the outlet chamber and allow the latter to move through the outlet conduit or frame to a second position that is on the ground and in which the ball can exit from the outlet chamber to the ground;
   introducing the ball into the outlet chamber;
   moving the outlet chamber to a second position using movement means connected to and configured to move said outlet chamber between at least the first position and the second position;
   using the launching means to apply pressure on the ball forcing it to exit the outlet chamber and enter onto the ground through the outlet mouth.

16. The method according to claim 15, further comprising applying ozone and/or ultraviolet light to the surface of the ball.

* * * * *